United States Patent [19]

Duffett

[11] Patent Number: Plant 5,365

[45] Date of Patent: Dec. 11, 1984

[54] CHRYSANTHEMUM PLANT NAMED ALERT

[75] Inventor: William E. Duffett, Salinas, Calif.

[73] Assignee: Yoder Brothers, Inc., Barberton, Ohio

[21] Appl. No.: 467,861

[22] Filed: Feb. 18, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Alert having flat capitulum form; daisy capitulum type; scarlet bronze ray floret color; diameter across face of capitulum ranging from 55 to 65 mm. at maturity; uniform eight week photoperiodic flowering response to short days; medium plant height when grown as a pinched spray pot mum; semi-upright branching pattern, and yellow green discs that remain pollen free.

3 Drawing Figures

1

The present invention comprises a new and distinct cultivar of *Chrysanthemum morifolium*, Ramat., named Alert.

Alert is a product of a planned breeding program which had the objective of creating new chrysanthemum cultivars for pinched, spray pot mum programs having daisy capitulum type, bronze floret color, eight week flowering response, and the ability to produce commercially acceptable quality in year round programs. Such traits in combination were not present or required improvement in previously available commercial cultivars.

Alert was originated from a cross made in a controlled breeding program in Salinas, Calif. in 1978. The female parent was an unnamed bronze daisy originated by the present inventor from a hybridization of two unnamed daisy seedlings. The male parent of Alert was an unnamed bronze daisy seedling originated from a cross between an unnamed bronze daisy seedling and Circus, disclosed in U.S. Plant Pat. No. 4,118.

Alert was discovered and selected as one flowering plant within the progeny of the stated cross by William E. Duffett in December 1979 in a controlled environment in Salinas, Calif.

The first act of asexual reproduction of Alert was accomplished when vegetative cuttings were taken from the initial selection in April 1980 in a controlled environment in Salinas, Calif. by a technician working under formulations established and supervised by William E. Duffett. Horticultural examination of selected units initiated April 1981 has demonstrated that the combination of characteristics as herein disclosed for Alert are firmly fixed and are retained through successive generations of asexual reproduction.

Alert has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial conditions.

The following traits have been repeatedly observed and are determined to be basic characteristics of Alert which in combination distinguish this chrysanthemum as a new and distinct cultivar:

2

(1) Flat capitulum form;

(2) Daisy capitulum type;

(3) Scarlet bronze ray floret color;

(4) Diameter across face of capitulum ranging from 55 to 65 mm. at maturity;

(5) Uniform eight week photoperiodic flowering response to short days;

(6) Medium plant height requiring 1-2 long day weeks prior to pinch and short days, and 1-2 applications of 12500 ppm B-9 after the beginning of short days to attain a flowered plant height of 25 to 35 cm.;

(7) Semi-upright branching pattern, and (8) Yellow green discs that remain pollen free.

The accompanying photographic drawings depict typical foliage and inflorescence characteristics of Alert. Sheet 1 is a color photograph of a plant of Alert grown as a pinched, spray pot mum, with colors being as accurate as possible with renditions of this type. Sheet 2 is a black and white photograph of three views of the inflorescence of Alert. Sheet 3 shows the leaves of Alert in three stages of development (mature, intermediate, immature).

Of the many commercial cultivars known to the present inventor, the most similar in comparison to Alert is Cirbronze, disclosed in U.S. Plant Pat. No. 4,492. Reference is made to attached Chart A which compares certain characteristics of Alert to those same characteristics of Cirbronze.

Alert displays much brighter bronze coloration, more upright branching pattern and one week shorter flowering response period. Cirbronze develops disc pollen; Alert does not. Cirbronze color oxidizes rapidly; Alert is more fade resistant. Cirbronze has similar capitulum size, form and type.

In the following description, color references are made to The Royal Horticultural Society Color Chart. The colour values were determined between 1:00 P.M. and 1:30 P.M. on Aug. 13, 1982 under 150 foot-candle light intensity at Salinas, Calif.

CLASSIFICATION

Botanical: *Chrysanthemum morifolium*, Ramat., cv Alert

Commercial: Spray daisy pot mum.

INFLORESCENCE

Capitulum:

*Form.*—Flat.

*Type.*—Daisy.

*Diameter across face.*—55 To 65 mm.

Corolla of ray florets:

*Color (general tonality from a distance of three meters).*—Scarlet bronze.

*Color (abaxial).*—Base 9B; length combines 34A and 169A.

*Color (adaxial).*—Base 9B; length combines 167C and 167B.

*Shape.*—Oblong. Rounded tip with slight notch.

Corolla of disc florets;

*Color (mature).*—14A.

*Color (immature).*—145A.

Reproductive organs:

*Androecium.*—Present disc florets only; scant pollen.

*Gynoecium.*—Present both ray and disc florets.

PLANT

General appearance:

*Height.*—Medium; 25 to 35 cm. given 2 long day weeks before pinch and lights out, and 1-2 applications of 2500 ppm B-9 SP after lights out.

*Branching pattern.*—Prolific; semi-upright.

Foliage:

*Color (abaxial).*—147A.

*Color (adaxial).*—147B.

*Shape.*—Deeply lobed. Coarsely serrate.

CHART A

COMPARISON OF ALERT AND CIRBRONZE

| CULTIVAR | RAY FLORET COLOR | CAPITULUM FORM AND TYPE | BRANCHING PATTERN |
|---|---|---|---|
| ALERT | SCARLET BRONZE | FLAT DAISY | SEMI-UPRIGHT |
| CIRBRONZE | MEDIUM BRONZE | FLAT DAISY | SEMI-SPREADING |

| CULTIVAR | DIAMETER ACROSS FACE OF CAPITULUM | PLANT HEIGHT | FLOWERING RESPONSE PERIOD |
|---|---|---|---|
| ALERT | 55 to 65 mm. | MEDIUM 25 to 35 cm. | 8 WEEKS |
| CIRBRONZE | 55 to 75 mm. | MEDIUM 30 to 40 cm. | 9 WEEKS |

COMPARISONS MADE OF PLANTS GROWN AS PINCHED SPRAY POT MUMS IN SALINAS, CALIFORNIA AND LEAMINGTON, CANADA

I claim:

1. A new and distinct cultivar of *Chrysanthemum morifolium,* Ramat., named Alert, as described and illustrated, and particularly characterized as to uniqueness by the combined characteristics of flat capitulum form; daisy capitulum type; scarlet bronze ray floret color; diameter across face of capitulum ranging from 55 to 65 mm. at maturity; uniform eight week flowering response; medium plant height; semi-upright branching pattern, and yellow green discs that remain pollen free.

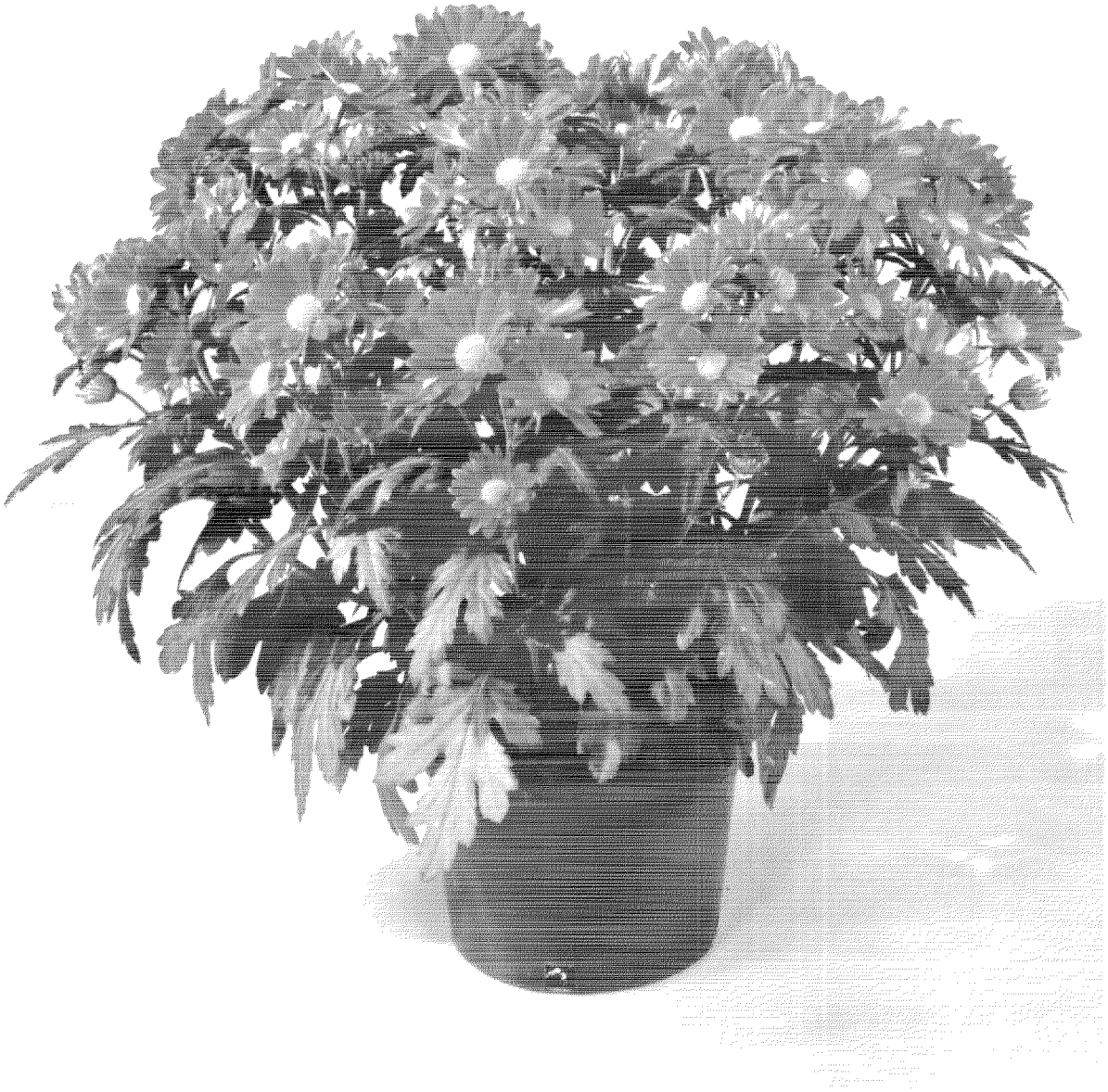

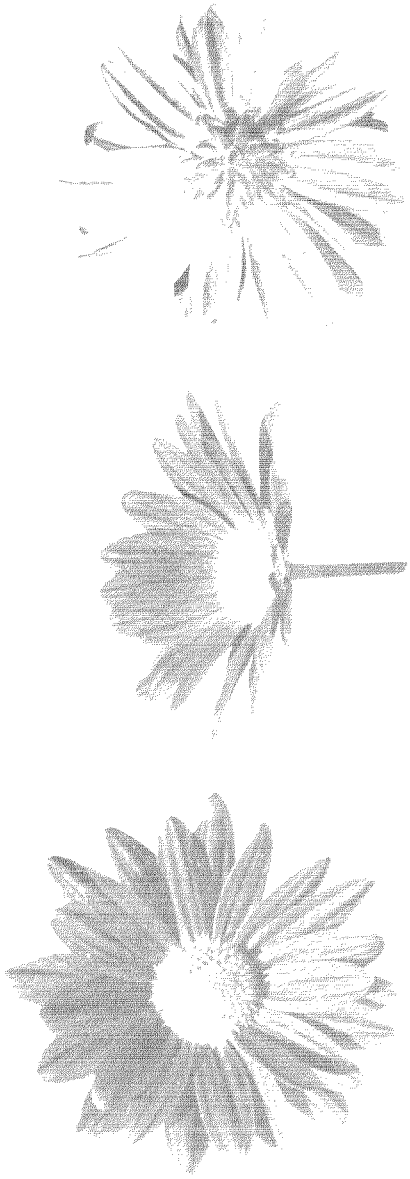

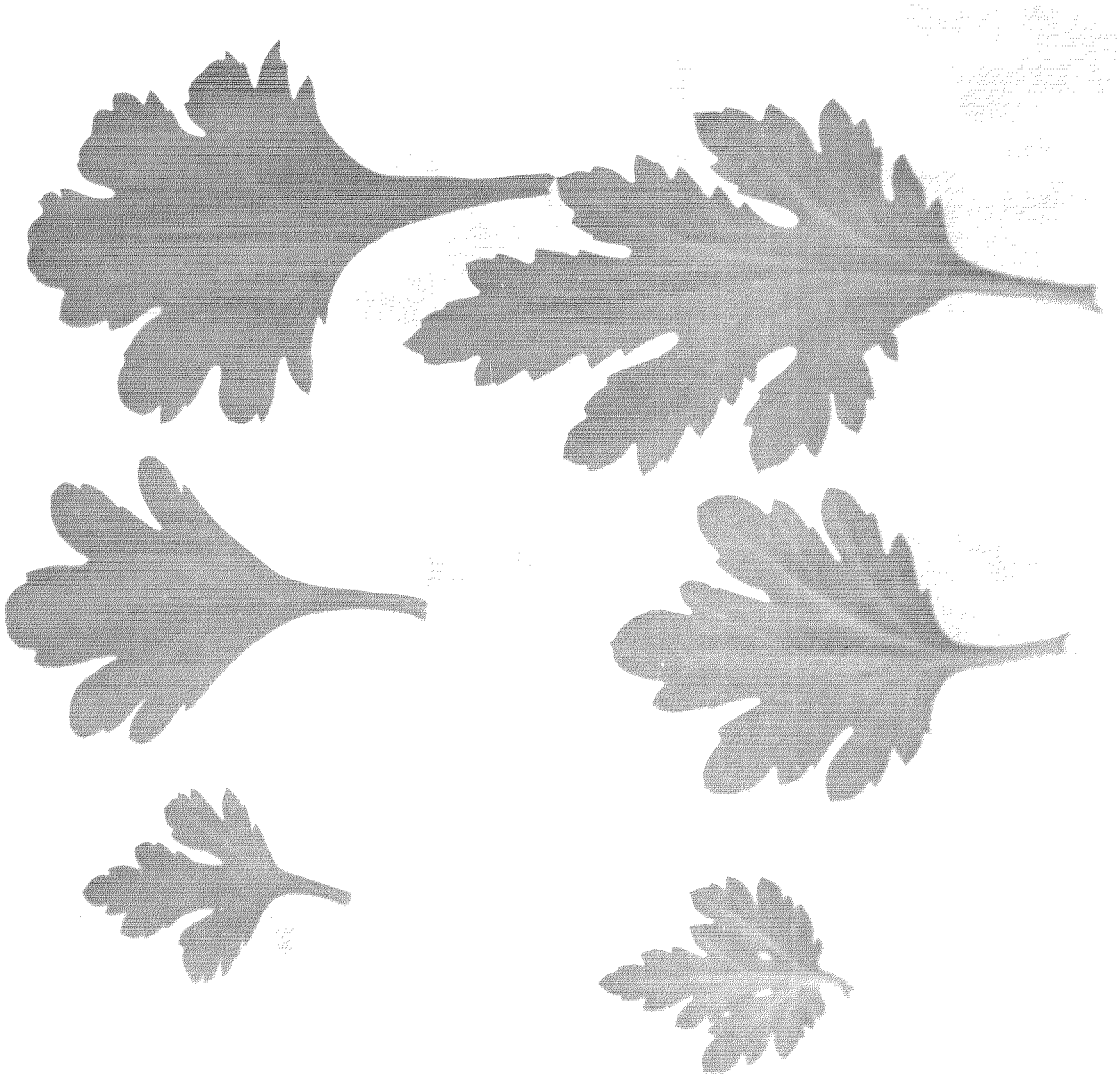

* * * * *